United States Patent
Cottrell (10) Patent No.: US 6,655,961 B2
(45) Date of Patent: Dec. 2, 2003

(54) MODIFIED DENTAL IMPLANT FIXTURE

(76) Inventor: Richard Day Cottrell, 119 E. Laurel, Unit 307, Lake Forest, IL (US) 60045

( * ) Notice: Subject to any disclaimer, the term of this patent is extended or adjusted under 35 U.S.C. 154(b) by 14 days.

(21) Appl. No.: 10/011,866

(22) Filed: Dec. 3, 2001

(65) Prior Publication Data

US 2003/0104337 A1 Jun. 5, 2003

(51) Int. Cl.⁷ .................................................. A61C 8/00
(52) U.S. Cl. ....................................... 433/173; 433/174
(58) Field of Search ................................ 433/172, 173, 433/174, 175, 176

(56) References Cited

U.S. PATENT DOCUMENTS

| | | |
|---|---|---|
| 5,030,095 A | 7/1991 | Niznick |
| 5,312,255 A | 5/1994 | Bauer |
| 5,362,236 A | 11/1994 | Branemark |
| 5,417,568 A | 5/1995 | Giglio |
| 5,503,558 A | 4/1996 | Clokie |
| 5,564,925 A | 10/1996 | Shampanier |
| 5,564,926 A | 10/1996 | Branemark |
| 5,702,695 A | 12/1997 | Clokie |
| 5,785,525 A | 7/1998 | Weissman |
| 5,863,201 A | 1/1999 | Lazzara et al. |
| 5,879,161 A * | 3/1999 | Lazzara ....................... 433/173 |
| 5,890,902 A | 4/1999 | Sapian |
| 5,947,735 A | 9/1999 | Day |
| 6,164,969 A * | 12/2000 | Dinkelacker ................. 433/173 |
| 6,217,333 B1 | 4/2001 | Ercoli |
| 6,283,754 B1 | 9/2001 | Wohrle |
| 2003/0031982 A1 * | 2/2003 | Abarno ........................ 433/173 |

OTHER PUBLICATIONS

Cawood and Howell, *Reconstructive Preprosthetic Surgery*, I. Anatomical considerations. Int. J. Oral Maxillofac. Surg. 1991; 20; 75–82.

* cited by examiner

Primary Examiner—Cary E. O'Connor
(74) Attorney, Agent, or Firm—Cook, Alex, McFarron, Manzo, Cummings & Mehler (57) ABSTRACT

A modified dental implant fixture designed to preserve lingual bone by having the coronal aspect of the implant being compatible with bony anatomy that is higher on the lingual side of the implant surgical site. The implant may be of either the single stage or the two stage design. By modifying the shape of the top of the implant fixture to mimic healing/healed bony anatomy, bone is preserved and bone growth is possibly encourage.

40 Claims, 5 Drawing Sheets

MODIFIED DENTAL IMPLANT FIXTURE

BACKGROUND OF THE INVENTION

The present invention relates generally to dental implants, and more specifically to a dental implant having an improved configuration to take advantage of the bone topography that is often present following tooth extraction.

Dental implants are used in place of missing and/or extracted natural teeth as the base of support for an abutment and final prosthesis in the attempt to restore normal oral function. Once teeth have been extracted, the alveolar bone at the extraction site heals and begins to undergo resorption. The resorption process is halted by restoring loading forces with a dental implant. The topographic changes of the alveolar bone have been described in the dental literature and are time dependent with regard to the amount of bone resorption. While implants are designed to replace natural teeth, they also must be designed to consider this natural healing of bone as well.

The implant body is surgically inserted in the patients jaw and becomes integrated with the bone. More specifically, the implant body is screwed or pressed into holes drilled in the respective bone. The surface of the implant body is characterized by macroscopic and microscopic features that aid in the process of osseointegration. Once the implant is fully integrated with the jaw bone, the abutment is ready to be mounted. For two-stage implant designs, the abutment passes through the soft tissue that covers the coronal end of the implant after healing and acts as the mounting feature for the prosthetic device to be used to restore oral function. Implants of the single-stage design extend through the tissue at the time of surgical insertion. The coronal end of the implant body acts as part of a built-in abutment design with the margin of the coronal collar usually used as the margin for the attachment of the prosthesis used to restore oral function. These components, the implant and abutment, are typically fabricated from titanium or an alloy of titanium as well as zirconia based, alumina based or sapphire based ceramics. In some instances, ceramics and metals are combined to make a single component, though this is usually limited to the abutment component of the implant system.

One of the major problems associated with dental implants stems from the failure to provide for the ideal alignment of implant fixtures in bone. Misalignment often results in the implant being positioned lingual to the ideal placement. Loosening or fracture of the abutments and even the implant body can result due to the adverse forces involved. Restorative dentists complain that the implants are not properly aligned by the surgeons, and the surgeons complain that the restorative dentists do not understand the challenges associated with the alignment process.

One of the most commonly placed fixture designs is the Branemark type implant. These implants are ideally positioned in the approximate center line of the space where the extracted tooth was previously position. As with most traditionally designed implants, the Branemark type fixture relies on a flat surface perpendicular to the long axis of the implant body for strength when joining the implant and the abutment together. This design usually displays a bone loss pattern described as a cupping of the bone at the coronal end of the implant once loaded with occlusal forces. This cupping pattern usually stabilizes after about one year of function with vertical bone loss of approximately 2 mm but, by that time, loss of bone critical to the predictable support of overlying soft tissue is lost.

Other implant systems often used are of the so called Astra Tech and ITI Straumann type implants. These implant designs have an internal conical connector and do not rely on perpendicular orientation of a flat surface for strength at the implant/abutment interface. Astra implants, due to or in combination with the rigid conical abutment connection and the presence of coronal stress reducing micro threads on the implant body, greatly reduce, and in some instances do not display the aforementioned bone loss patterns. However, the problem still exists as to the misalignment of such implants due to the flat topped coronal feature of the implant body in its present configuration.

Astra Tech has addressed coronal bone loss by introducing micro threads at the coronal portion of the implant body to distribute forces transferred to the surrounding bone. Other attempts to enhance implant designs have addressed bone loss patterns and lack of soft tissue support by focusing on the coronal aspect of the implant body in hopes of mimicking natural CEJ (cemento-enamel junction) anatomy or shaping the implant body to be more root line in character. Implants duplicating tooth anatomy in some way, shape or form have not had the same level of success as the Astra Tech concept. Unfortunately, once the tooth has been extracted, the bone does not remember what the tooth looked like, or what function it provided. Still, even with the Astra's success, the design of the implant fixture and how that design interacts with the bony anatomy at the surgical site has not been addressed correctly. To date, no design has considered the anatomy of how bone heals in the human jaw following tooth extraction.

Accordingly, it is a general object of the present invention to provide an improved implant such that many of the problems related to implant placement are eliminated.

It is a more specific object of the present invention to enable implants to be placed in surgical sites of sloping bony anatomy more predictably.

Another object of the present invention is to preserve lingual bone by having the coronal aspect of the implant being compatible with the bony anatomy that is higher on the lingual side of the surgical site.

It is another object of the present invention to provide for increased strength of the implant/abutment system.

Yet another object of the present invention is to reduce the amount of time required by the restorative dentist to prepare and idealize the abutment.

Another object of the present invention is to reduce the number of abutment orientation surfaces, thereby reducing the size requirement for the implant body.

Still another object of the present invention is to make the use of snap on impression caps more useful and resulting in the final prosthesis being more functional and cosmetic in appearance.

Yet another object of the present invention is to allow for a single implant to be placed in the anterior region of the human jaw with predictable soft tissue contours supported by bone.

Still another object of the present invention is to allow multiple implants to be placed more predictably next to one another in the anterior region of the human jaw.

SUMMARY OF THE INVENTION

According to the present invention, there is provided a dental implant for implanting within a human jawbone, the jawbone having lingual and buccal sides. The implant includes a generally cylindrical longitudinal body having apical and coronal ends and an outer surface. The length of the body is defined by the ends along the outer surface. The coronal end is contoured such that the length of the body is greatest on the lingual side of the jaw when positioned within the bone.

BRIEF DESCRIPTION OF THE DRAWINGS

The features of the present invention, which are believed to be novel, are set forth with particularity in the appended claims. The invention, together with the further objects and advantages thereof, may best be understood by reference to the following descriptions take in conjunction with the accompanying drawings, in the several figures of which like reference numerals identify like elements, and in which:

DESCRIPTION OF THE PREFERRED EMBODIMENT

Dental implants are used in place of missing and/or extracted natural teeth as the base of support for an abutment and final prosthesis in the attempt to restore normal oral function. Implants have therefore been designed by attempting to mimic these missing natural teeth. However, once a tooth has been extracted, the bone from which the tooth originated heals and is forever changed and probably continuously changing due to the forces exerted on it. As these implants are designed to replace natural teeth, they need to be designed for the natural healing bone as well.

Figure 1:
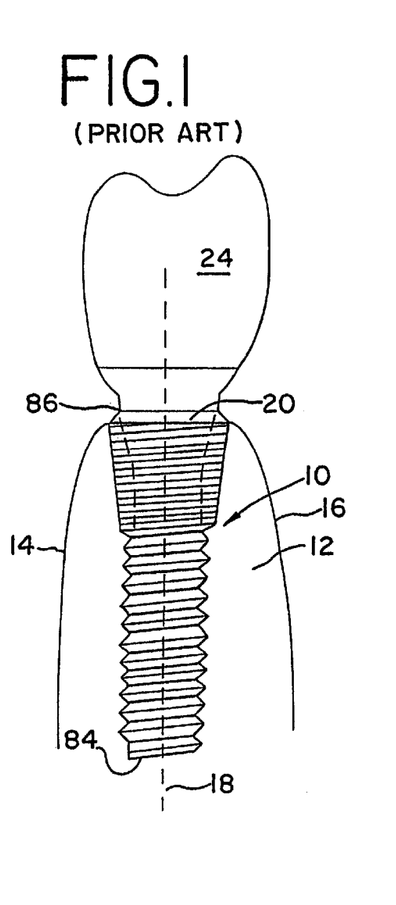
FIG. 1 is a side view of the ideal implant placement within the jaw bone.

Referring now to the Figures, and in particular FIG. 1, a typical implant 10 is illustrated implanted within the jaw bone 12. For purposed of describing the invention, the bone 12 of the human jaw will primarily be discussed with respect to its lingual 14 and buccal 16 sides. This bone 12 illustrated by FIG. 1 is that of an ideal, but infrequent implant site. That is, lingual side 14 and buccal side 16 bone appear to be comparable in height and shape with respect to the center 18 of the maximum height of available bone. Therefore, the typical implant 10, with its flat top or coronal aspect 20 is suitable for its intended purpose when implanted within such a jaw bone condition.

However, when teeth are extracted, this ideal bone site of FIG. 1 is seen more frequently in drawings from implant manufacturers rather than at the actual surgical sites encountered during surgical placement of implant fixtures. This is because the bone does not heal evenly once a tooth has been extracted. It has been found that bone heals based on the principles of bone biology and surrounding bony anatomy. To a degree, bone healing and/or remodeling is influenced by the placement and subsequent loading of an implant fixture in the area of the extracted tooth or teeth. In fact, a number of studies have been conducted regarding bone loss patterns. One such study, by Cawood and Howell was published in the *International Journal of Oral and Maxillofacial Surgery* in 1991.

This study analyzed patterns of alveolar bone resorption from a sample of 300 dried skulls with edentulous jaws. In general, bone loss is four times greater in mandible than the maxilla. One can construe from this study that the highest point of bone anatomy is at the lingual side of the extracted teeth after healing for a time period even as short as several months. Due to the natural bony contours in the anterior area of the upper and lower jaws, this healing pattern, often referred to as facial collapse of bone, is more immediate than in the posterior upper and lower jaws. If an implant fixture is placed in the center of the maximum height of available bone, the implant can end up too far to the lingual from the point of view of the restorative dentist.

Figure 2:
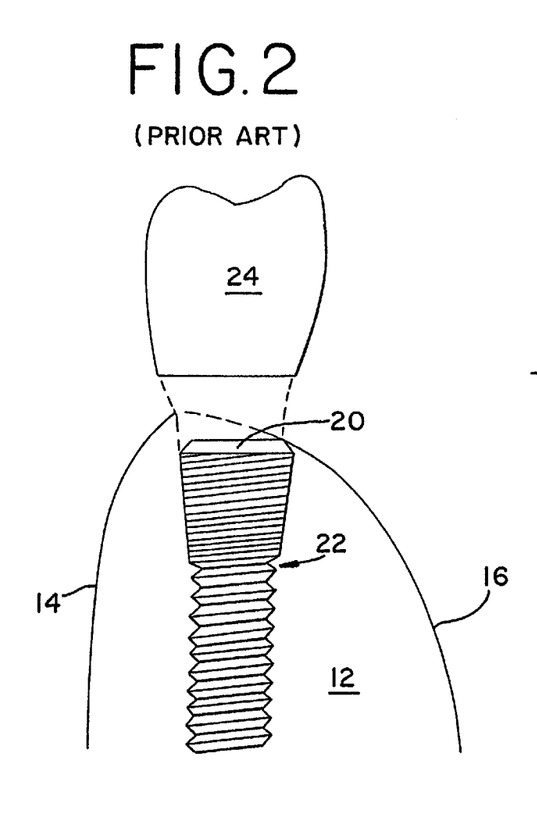
FIG. 2 is a side view of the ideal alignment of a typical implant buried within the jaw bone with sloping topographic anatomy to avoid fixture thread exposure.

To avoid this overly lingual placement, implants can be submerged even to the facial level of bone. FIG. 2 is illustrative of such a submersion as the implant 22 is shown with its coronal aspect 20 fully submerged on the lingual side 14 and even with the bone 12 on the buccal side 16. The crown 24 to be attached to the abutment is then affixed to the coronal aspect 20 in an attempt to restore normal oral function. As such an implant needs to be buried within the bone to compensate for the shape of the healing bone, the implant 22 must be significantly shorter in length than the ideal size shown in FIG. 1. This results in a weaker and less stable implant/abutment complex.

Figure 3:
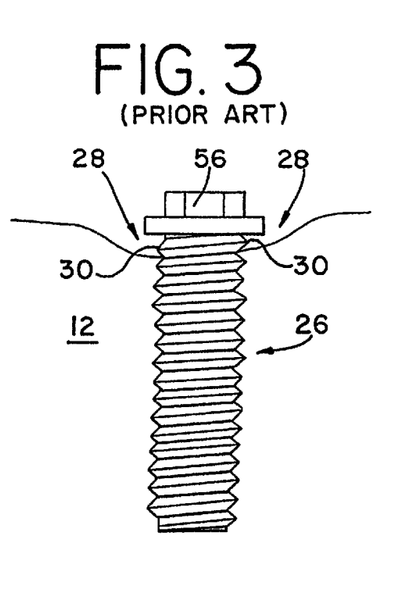
FIG. 3 is a front view of a Branemark type implant design showing typical cupping bone loss at the coronal aspect of the implant after loading with functional forces.

Another problem with burying implants is illustrated by FIG. 3. This Figure shows a typical Branemark type implant 26 which was previously buried within the bone 12 as discussed above. After the implant has been affixed with an abutment and crown, the loading forces typically produce a bone loss pattern referred to as cupping 28. This bone loss usually exposes the threads 30, and, essentially, results in the placement of what amounts to be a shorter implant and thus a weaker implant in the jaw bone.

Figure 4:
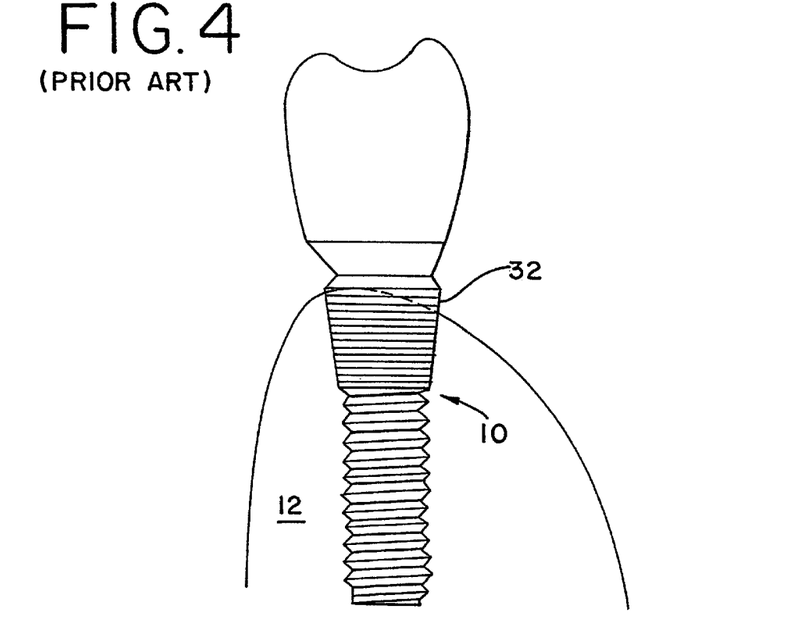
FIG. 4 is a side view of the ideal alignment of a typical implant within the jaw bone with sloping topographic anatomy having threads exposed on the facial aspect of the implant body.

Another way to avoid overly lingual implant placement is illustrated by FIG. 4. Here, the implant 10 has been inserted into the bone 12 with the proper alignment (as it had in FIG. 2), but now the implant is protruding due to the sloping bony anatomy. Maximum height of available bone was engaged, but exposed threads 32 compromise the ideal facial contour of the final restoration.

Figure 5:
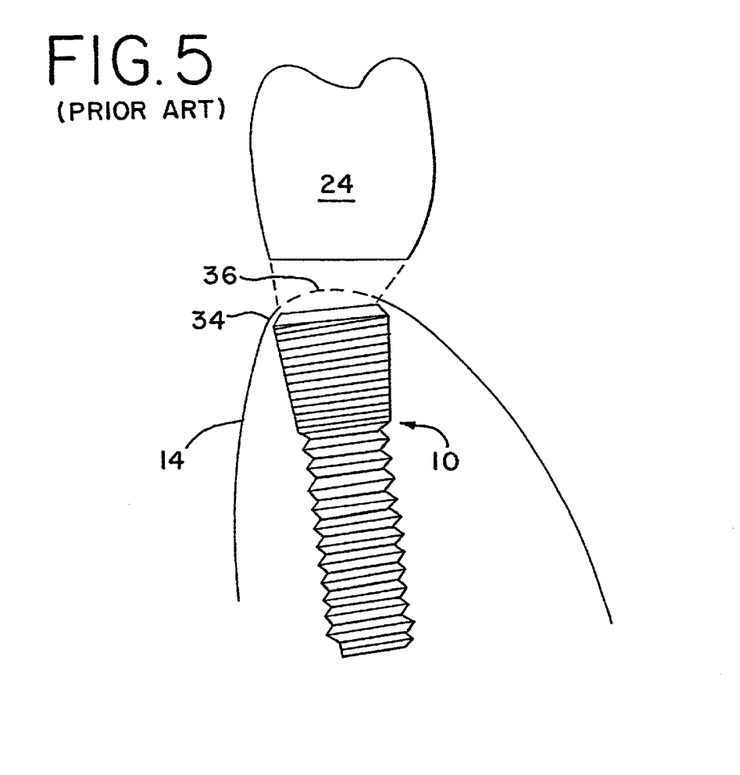
FIG. 5 is a side view of the typical implant placed within the center of the maximum available bone height.

While the positioning of the implant is improved by burying or protruding same, supporting bone is compromised in one instance (FIG. 2) and poor gingival profile results within the other placement (FIG. 4). In an attempt to avoid these problems in the mandible, surgeons may opt to misalign the implant by angling its position as shown in FIG. 5. Here, the implant is angled towards the lingual to avoid perforating the lingual plate of bone 34. In other words, the implant 10 is placed in the middle of the highest point of bone 36 lingual to where the missing tooth was previously positioned. Thus, this kind of positioning may create the greatest problem for the restoring dentist as he now must attempt to esthetically and functionally position the crown 24 and abutment.

Proper alignment of the dental implant is essential to the esthetics as well as the mechanics of proper oral function. If the abutment and crown are affixed to a misaligned implant, the tooth not only looks unattractive, but it will not be able to function properly as unfavorable loading forces will exist. Referring back to FIGS. 1–5, FIG. 1 shows a properly aligned implant 10 and thus and thus a properly aligned crown 24. FIGS. 2 and 4 show proper alignment of the implant, but demonstrate other problems previously described. Finally, FIG. 5 shows an improperly aligned implant and thus a crown affixed to the buccal of the implant fixture Since the Astra Tech type implants do not have a flat coronal aspect that is integral to the abutment connection, it is possible to shape the coronal contours to mimic healing/healed bony anatomy at the implant surgical site. Additionally, because Astra Tech implants do not loose coronal bone as do the Branemark type implants, it is possible to preserve and possibly encourage slight bone growth in the coronal direction. By preserving lingual bone height, bone mesial and distal to the implant will also be maintained because, according to studies, including Cawood and Howell, bone slopes apically from the lingual. Preserve the lingual bone, and more bone adjacent to the implant on the mesial and distal sides will be preserved. This is critical if predictable soft tissue papilla overlying these hard tissue sites is to be generated or maintained. It has been shown that only 4 mm of papilla height over mesial and distal bone is considered a level that the restorative dentist can rely on being generated time and again. Without surrounding esthetic papilla, even the most perfectly contoured crown is unsightly in the upper anterior region of the mouth.

Figure 6:
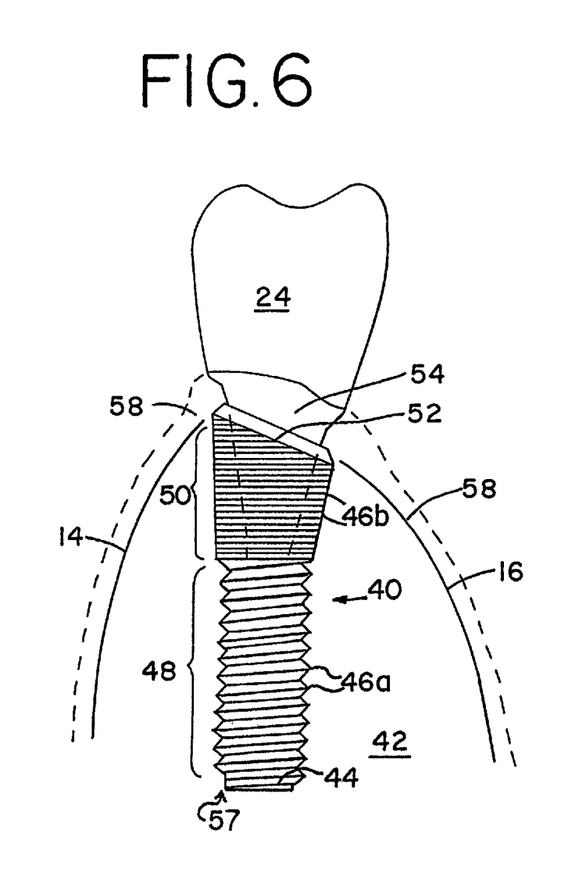
FIG. 6 is a side view of the preferred embodiment of the implant of the present invention.

The preferred embodiment of the present invention is illustrated by FIG. 6. The implant 40 is a cylindrical longitudinal structure designed for bone 42 engagement. The typical length 82 (FIG. 9) of the preferred embodiment is much like the currently used implants. That being between 9 to 18 mm base 84 to top 86 (FIG. 1) while the typical diameter is between 3 to 6.5 mm base 84 to top 86. The body of the implant 40 is preferably, but need not be, comprised of screw threads 46a and/or 46b to aid in the implantation process. The lower apical half 48 of the implant body includes larger threads 46a than the smaller threads 46b of the upper (coronal) half 50. It has been found that the smaller threads 46b significantly reduce stress forces transmitted to bone and helps to preserve cortical bone. They also increase the fixture strength by adding wall thickness without changing the outer dimension of the implant. However, other means many be used on the outside surface of the implant 40 affixed to the implant within the bone 42, so long as the apical end 44 thereof is securely anchored. The surface of the implant 40 may be texture coated in differing ways to promote osseointegration.

The coronal end 52 of the implant 40 accepts the base of the prosthetic abutment 54 using connection mechanisms of different designs. An example of such a design is the hex shape 56 shown on the implant 26 of FIG. 3. While the commonly used internal hex or twelve position internal star design can be used, other options are now possible since the implant design has one vs. multiple orientations. Three to five sided abutment alignment surfaces with from three to twelve internal designs are feasible; even one or two alignment surfaces are possible. Reducing the number of abutment orientation surfaces reduces the size requirements for this feature of the implant body. This is important in developing smaller fixtures suitable for use to replace lower anterior teeth.

The basic concept of the present invention is the contouring or sloping of the coronal 52 or top of the implant fixture such that lingual bone 14 is engaged and preserved. This coronal contour can be a straight line or a slightly convex contoured design so long as one bone engaging side 57 of the implant body (which would become the lingually oriented side of the implant fixture) is longer in the apical-coronal bone engaging dimension than any other apical-coronal bone engaging dimension. This apical-coronal dimension or lingual high point does not include any implant collar (if present), but only the bone engaging surface of the implant since the invention primarily addresses bone preservation with predictable soft tissue preservation being understood to be dependent on maintaining underlying supporting bone. Biomechanics are improved for the entire implant 40 abutment 54 and crown 24 complex. Soft tissues 58 are much more predictable since underlying support bone is preserved.

Surgeons will be much less inclined to place fixtures at the middle of the maximum height of available bone which is often to the lingual of the desired implant position (see FIG. 5). The sloping surface of the coronal 52 makes it much more likely that placement in the center of the space formerly occupied by the missing tooth will be possible. Because the lingual aspect of the implant 40 can be placed more coronally without the compromise inherent with flat top designs (See FIGS. 2–5), a more favorable implant fixture to prosthesis ratio results which improves stress distribution. Furthermore, the design of the present invention does not reduce the strength of the implant, but in fact makes it stronger by extending the lingual side of the fixture coronally. The implant fixture, when surgically placed, is longer by the height of the lingual coronal extension, but is not placed deeper in the jaw bone.

Figure 7:
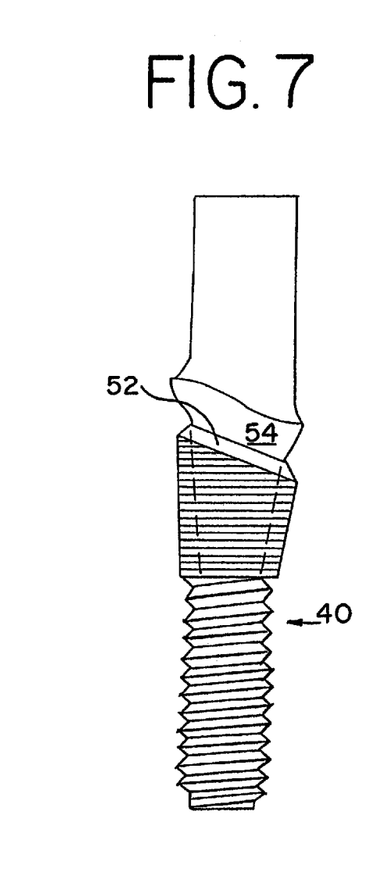
FIG. 7 is an elevated side view of another embodiment of the implant of the present invention with a small sized contoured abutment attached coronally.
Figure 8:
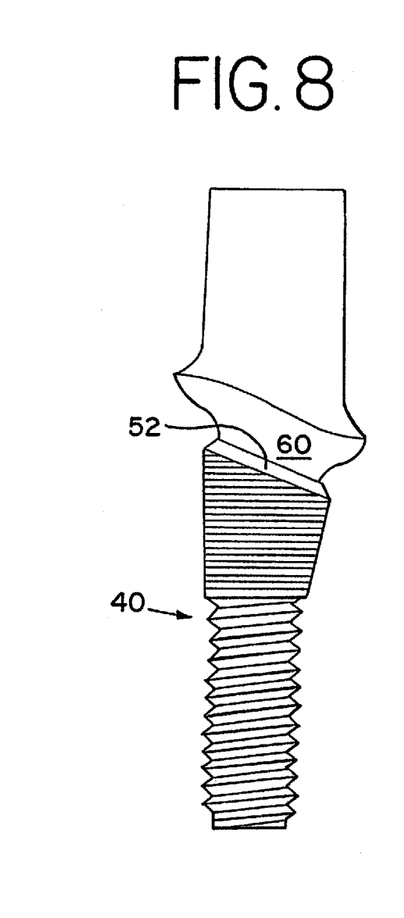
FIG. 8 is an elevated side view of another embodiment of the implant of the present invention with a large sized contoured abutment attached coronally.

Referring now to FIG. 7, the abutment 54 design simulates or follows natural tissue contours 58 because of the coronal sloping 52 feature of the implant. This dramatically reduces the amount of time required by the restorative dentist to prepare and idealize the abutments. Similarly, FIG. 8 shows a contoured abutment 60 of a larger size, which may be more suited for a molar tooth. In any event, the designs of FIGS. 7 and 8, or any similar designs that have tissue or gingival contour to take advantage of the coronal contour of the implant body, will enable the restorative dentist to idealize final margin placement rapidly.

Figure 9:
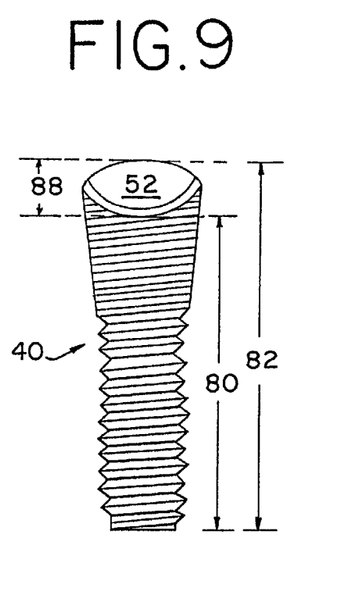
FIG. 9 is an elevated front view of the preferred embodiment of the implant of the present invention.

The contouring or sloping of the coronal 52 or top of the implant fixture may best be illustrated by FIG. 9. Here, the differential bone-engaging surface of the implant 40 is shown with respect to its buccal length ($L_1$) 80 in comparison to its lingual length ($L_2$) 82. While the preferred contour may differ from patient to patient, preferably the height differential ($L_2-L_1$) 88 is between 1 and 4 mm, more preferably this differential 88 is between 2 and 3 mm. Therefore, as is shown, the bone-engaging surface, or the outer surface of the implant which is in contact with the jaw, of the implant 40 is longer on one side (lingual) than the other. With such a shape, bone preservation throughout the jaw is achieved.

Figure 10:
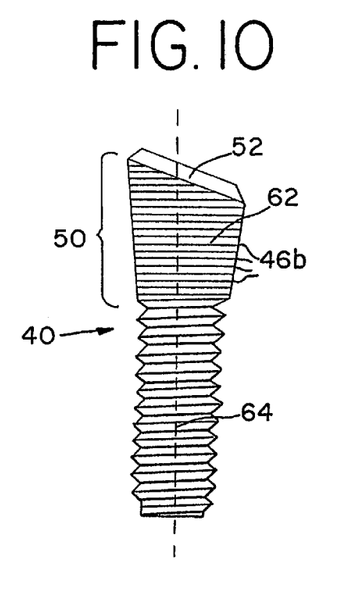
FIGS. 10–12 are elevated side views of similar embodiments of the present invention.
Figure 11:
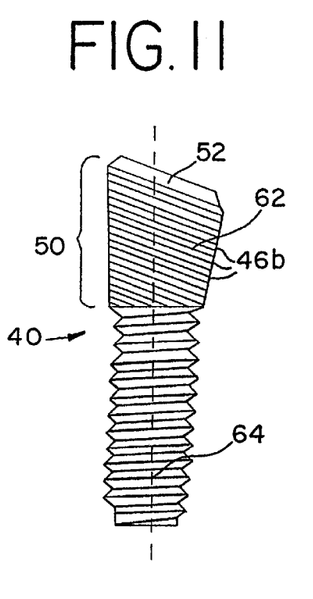
Figure 12:
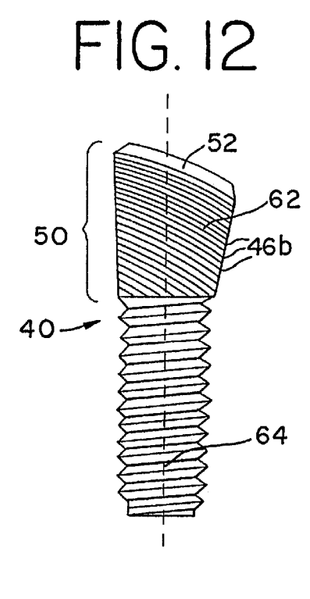

The coronal end 50 of the implant body 40 is preferably characterized by textured grit blasting 62 with or without micro threads/grooves 46b as shown in FIG. 10. If micro threads/grooves are evident, they may be perpendicular (FIG. 10) to the long axis 64 of the implant 40, or parallel to the sloped (FIG. 11) or convex (FIG. 12) coronal contour 52. Having the micro threads 46b parallel to the coronal contour 52 as in FIGS. 11 and 12 may further aid in bone preservation and possibly coronal bone apposition.

Figure 13:
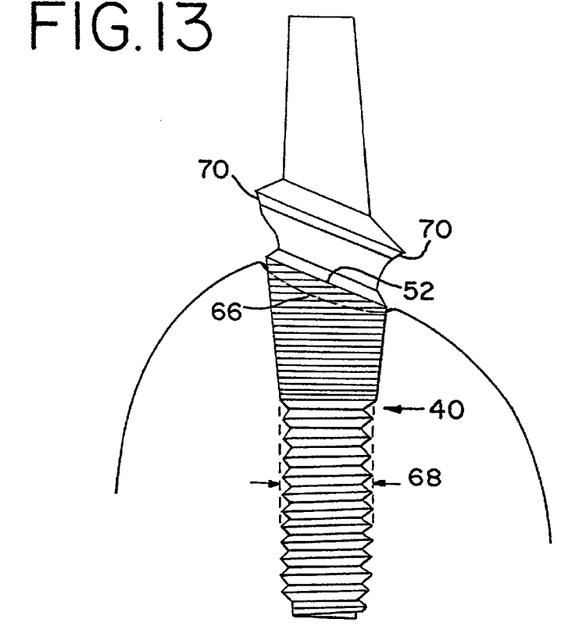
FIG. 13 is a side view of the preferred embodiment of the implant of the present invention of the two stage type design with an abutment designed to be used with snap-on impression caps.

FIG. 13, like FIGS. 6–12, illustrates a design of the present invention as it relates to a two-stage type implant. The body 40 of the implant is widest at the most coronal bone engaging aspect 66 and narrows moving apically before having parallel walls 68 in the apical half of the fixture. This inward coronal feature allows for thicker bone surrounding the implant coronally, while at the same time creating adequate coronal width to resist mechanical occlusal loading. The two-stage design of FIG. 13 takes advantage of the sloped coronal surface 52 and enables the use of a snap-on impression caps. These impression caps engage the undercut 70 of the abutment margins.

Figure 14:
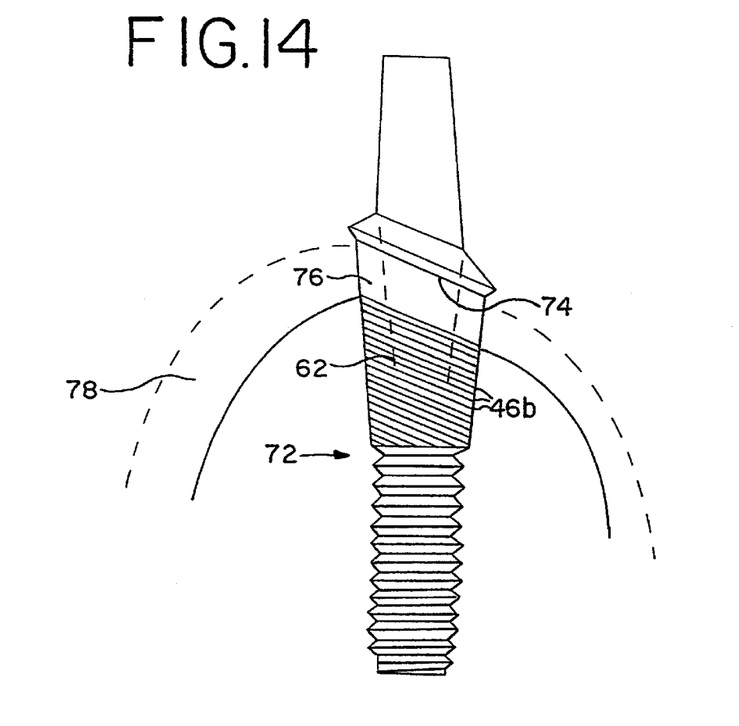
FIG. 14 is a side view of the preferred embodiment of the implant of the present invention of the single stage type configured to be used with snap-on impression caps.

FIG. 14, unlike FIGS. 6–12, illustrates a design of the present invention as it relates to a single stage type implant. This implant 72 also incorporates the sloped coronal 74 contours of the aforementioned designs. All advantages that apply to the two stage implant design apply to this design as well. A machined collar 76 coronal to the micro threads 46b and/or the grit blasted surface 62 does not engage bone (the non-bone engaging surface of the implant) and passes through the soft tissue 78. This design allows for snap on impression caps (as described above) deemed essential to single stage designs. The perfect alignment afforded to the implants of FIGS. 13 and 14, due to the sloping coronal 52, provide for the perfect environment for snap-on impression caps.

Whether utilizing a single stage or a two-stage type implant, the basic methodology for the surgeon remains the same. First, the implant site is chosen. This is preferably the site where the extracted tooth originated, but, depending upon the length of time that has lapsed since the extraction, this site may be more lingual than the ideal. Next, the physical design for the shape and size for the implant is chosen. This is dependent upon the remaining jawbone shape and size as well as other factors. This design will include overall length as well as coronal differential, among others. Then, with the size and shape of the bone and the implant known, an approximate number of rotations is determined for the ideal penetration of the screw/thread type implant. In other words, and for example, assuming that one complete 360° rotation of the implant results in a X mm penetration within the bone, the surgeon can then determine that Y rotations will result in the ideal penetration and positioning of the implant. With a two-stage implant, this results in a penetration such that the coronal end of the implant is flush to bone; whereas the coronal end will be above the bone with a single stage implant. Now, the surgeon positions the implant at the (preferably pre-drilled) site and with Y rotations, has properly implanted his patient.

The present invention provides for great latitude to the surgeon with respect to placement of these implants. For example, single implants placed in the esthetic zone (upper anterior) will be much more predictable in outcome since soft tissue supporting bone mesial and distal of the implant body is preserved since bone on the lingual aspect of the fixture is not sacrificed or compromised. Similarly, the fixture design allows multiple implants to be placed in the esthetic zone, including implants placed next to one another, much more predictable when this is attempted with typical flat top designs. Since inter-implant bone is essentially preserved by the height of the lingual bone which is not sacrificed or compromised, papilla are maintained in the spaces between final individual implant supported restorations.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A two-stage dental implant for implanting within a human jawbone, the jawbone having lingual and buccal sides, the implant comprising:

a generally cylindrical longitudinal body having an apical end, a coronal end and an outer surface;

said body having a length defined between said ends on said outer surface; and said coronal end being contoured such that when positioned within the jawbone, said length is greatest on the generally lingual side and least on the generally buccal side such that said length generally decreases from lingual to buccal.

2. A dental implant as defined in claim 1, wherein said body has a diameter and includes at least one size of grooves around said diameter on at least a portion of said body.

3. A dental implant as defined in claim 2, wherein said grooves are parallel with the contour of said coronal end.

4. A dental implant as defined in claim 2, wherein said grooves are perpendicular to said length of said implant body.

5. A dental implant as defined in claim 4, wherein said grooves on the coronal part of the implant body have multiple leading starting points to allow synchronization with larger apical grooves.

6. A dental implant as defined in claim 1, wherein said coronal end is adapted to accept an abutment.

7. A dental implant as defined in claim 6, wherein said abutment is contoured to generally follow said contour of said coronal end.

8. A dental implant as defined in claim 6, wherein said abutment includes margins adapted to engage an impression cap.

9. A dental implant as defined in claim 6, wherein said abutment extends coronally with off axis angulation.

10. A dental implant as defined in claim 1, wherein said contour is straight.

11. A dental implant as defined in claim 1, wherein said contour is convex.

12. A dental implant fixture as defined in claim 1, wherein said contour is textured.

13. A dental implant as defined in claim 1, wherein said body is widest at said coronal end and narrows to parallel surfaces apically.

14. A two-stage dental implant for implanting within the human jawbone, the jawbone having lingual and buccal sides, the implant comprising:

a generally cylindrical longitudinal body having an apical end, a coronal end and an outer surface;

said body having a bone engaging surface defined between said ends; and said coronal end being contoured such that when positioned within the jawbone said bone engaging surface is longest/greatest on the generally lingual side and shortest/least on the generally buccal side such that said bone engaging surface decreases from lingual to buccal.

15. a dental implant as defined in claim 14, wherein said coronal end is adapted to accept an abutment.

16. A dental implant as defined in claim 15, wherein said abutment is contoured to generally follow said contour of said end.

17. A dental implant as defined in claim 15, wherein said abutment includes margins adapted to engage an impression cap.

18. A dental implant as defined in claim 14, wherein said abutment extends coronally with off axis angulation.

19. A single-stage dental implant for implanting within the human jawbone, the jawbone having lingual and buccal sides, the implant comprising:
  a generally cylindrical longitudinal body having an apical end, a coronal end and an outer surface;
  said body having a bone engaging surface defined between said ends;
  said coronal end being contoured such that the bone engaging surface is prepared to be longest/greatest on the generally lingual side and shortest/least on the generally buccal side such that said bone engaging surface decreases from lingual to buccal when positioned within the jawbone; and
  said body also having a non-bone engaging surface extending coronally from said bone engaging surface whereby said non-bone engaging surface when combined with said bone engaging surface is longest/greatest on the lingual side.

20. A dental implant as defined in claims 14 or 19, wherein said body has a diameter and includes at least one size of grooves or threads around said diameter on at least a portion of said body.

21. A dental implant as defined in claim 20, wherein said grooves or threads are parallel with and adjacent to the contour of said coronal end.

22. A dental implant as defined in claim 20, wherein said grooves or threads are perpendicular to the long axis of the implant body and adjacent to the contour of said coronal end.

23. A dental implant as defined in claim 22, wherein said grooves on the coronal part of the implant body have multiple leading starting points to allow synchronization with larger apical grooves.

24. A dental implant as defined in claims 14 or 19, wherein grit blasting or other surface texturing designed to promote osseointegration is used on the coronal aspect of all bone engaging surfaces.

25. A dental implant as defined in claim 19, wherein said coronal end is adapted to accept an abutment extending coronally with or without angulation.

26. A dental implant as defined in claim 25, wherein the coronal margin of the implant is adapted to engage an impression cap fitting over the abutment.

27. A dental implant as defined in claims 14 or 19, wherein said coronal contour is straight.

28. A dental implant as defined in claims 14 or 19, wherein said coronal contour is convex.

29. A dental implant as defined in claims 14 or 19, wherein said bone engaging surface is textured.

30. A dental implant as defined in claims 14 or 19, wherein said body is widest at said coronal end and narrows to parallel surfaces apically.

31. A dental implant as defined in claims 14 or 19, wherein said body has threads on the apical portion of said body.

32. A dental implant for implanting within the human jawbone, the jawbone having lingual and buccal sides, the implant comprising:
  a generally cylindrical longitudinal body having an apical end and a coronal end; and
  said body having a bone engaging portion defined between said ends of a defined length, said coronal end of said bone engaging portion having a coronal facing generally asymmetric truncated cylindrical surface such that said bone engaging portion generally decreases in length from lingual to buccal.

33. A dental implant as defined in claim 32, wherein said asymmetrical truncated cylindrical surface has a lingual side surface and a buccal side surface and said defined length between said apical end and said lingual side surface is between around 1 mm to 4 mm longer in length than said defined length between said apical end and said buccal side surface.

34. A dental implant as defined in claim 33, wherein said defined length between said apical end and said lingual side surface is around 2 mm to around 3 mm longer in length than said defined length between said apical end and said buccal side surface.

35. A dental implant as defined in claim 34, wherein said defined length between said apical end and said lingual side surface is around 2 mm longer in length than said defined length between said apical end and said buccal side surface.

36. A dental implant as defined in claim 32, wherein said generally asymmetrical truncated cylindrical surface is contoured.

37. A dental implant as defined in claim 36, wherein said contour is slightly convex.

38. A method for implanting a screw/thread type dental fixture within the human jawbone, the fixture having a coronal end, the method comprising:
  determining a correct implant site;
  determining a correct physical implant design;
  pre-drilling said site for said implant;
  determining an approximate number of rotations of said implant for an ideal penetration within the jawbone; and
  screwing the implant into the jawbone by rotating said implant said approximate number of rotations, such that said implant achieves said ideal penetration.

39. A method of implanting a screw/thread type dental fixture as defined in claim 38, wherein said ideal penetration is such that the coronal end is flush with the jawbone.

40. A method for implanting a screw/thread type dental fixture as defined in claim 38, wherein said ideal penetration is such that the coronal end is above the jawbone.

* * * * *